(12) United States Patent
Sugo et al.

(10) Patent No.: US 6,811,771 B1
(45) Date of Patent: Nov. 2, 2004

(54) BACTERICIDAL ORGANIC POLYMERIC MATERIAL

(75) Inventors: Takanobu Sugo, Gunma (JP); Kazuyoshi Takeda, Kanagawa (JP); Kunio Fujiwara, Kanagawa (JP); Tadashi Adachi, Tokyo (JP); Hideo Kawazu, Kanagawa (JP); Makoto Komatsu, Kanagawa (JP); Junichi Kanno, Kanagawa (JP); Takeshi Takai, Kanagawa (JP)

(73) Assignees: Ebara Corporation, Tokyo (JP); Japan Atomic Energy Research Institute, Tokyo (JP)

( * ) Notice: Subject to any disclaimer, the term of this patent is extended or adjusted under 35 U.S.C. 154(b) by 0 days.

(21) Appl. No.: 09/926,400

(22) PCT Filed: Apr. 25, 2000

(86) PCT No.: PCT/JP00/02700

§ 371 (c)(1),
(2), (4) Date: Jan. 30, 2002

(87) PCT Pub. No.: WO00/64264

PCT Pub. Date: Nov. 2, 2000

(30) Foreign Application Priority Data

Apr. 27, 1999 (JP) .......................................... 11/119200

(51) Int. Cl.[7] ........................ A61K 31/74; A61K 47/48; A61K 31/79

(52) U.S. Cl. .................. 424/78.17; 42/78.18; 42/78.24; 42/78.25; 42/78.27

(58) Field of Search .......................... 424/78.27, 78.31, 424/78.17, 78.18, 78.24, 78.25, 78.35, 669, 667, 672, 78.07, 78.06

(56) References Cited

U.S. PATENT DOCUMENTS 2,706,701 A    4/1955 Beller et al.
2,739,922 A    3/1956 Shelanski
2,826,532 A    3/1958 Hosmer
2,900,305 A    8/1959 Siggia
3,028,300 A    4/1962 Cantor et al.
3,898,326 A    8/1975 Cantor et al.
4,407,846 A   10/1983 Machi et al.
5,684,042 A  * 11/1997 Greff et al. .................. 514/527

FOREIGN PATENT DOCUMENTS

| JP | 48-34701 | 10/1973 |
|----|----------|---------|
| JP | 51-74083 | 6/1976 |
| JP | 55-102633 | 8/1980 |
| JP | 56-136456 | 10/1981 |
| JP | 8-72612 | 2/1996 |
| JP | 9-290272 | * 11/1997 |
| JP | 11-241088 | 9/1999 |
| WO | WO 85/02422 | * 6/1985 |
| WO | 85/02422 | 6/1997 |

OTHER PUBLICATIONS

Whittington's Dictionary of Plastics by Whittington, Lloyd R., p. 13.*
Plastics Technology Handbook by Chanda, Manas and Roy, Salil K., p. 18, chapter 1.*
Hans–Uwe Schenck et al.: "Structure of Polyvinylpyrrolidone–Iodine (Povidine–Iodine)" Journal of Pharmaceutical Schiences, vol. 68, No. 12, pp. 1505–1509 12/79.

* cited by examiner

*Primary Examiner*—Gollamudi S. Kishore
*Assistant Examiner*—Blessing M. Fubara
(74) *Attorney, Agent, or Firm*—Oblon, Spivak, McClelland, Maier & Neustadt, P.C.

(57) ABSTRACT

An object of the present invention is to provide a filter material capable of killing microorganisms, bacteria, fungi or viruses in air or liquids. Antimicrobial organic polymer materials of the present invention comprise an organic polymer material having a polymer side chain containing a unit derived from an N-alkyl-N-vinylalkylamide on a backbone of a polymer substrate, wherein triiodide ion is carried on said organic polymer material.

25 Claims, 1 Drawing Sheet

W: Inhibition circle width
L: Inhibition circle diameter
T: Test piece diameter

W: Inhibition circle width
L: Inhibition circle diameter
T: Test piece diameter

BACTERICIDAL ORGANIC POLYMERIC MATERIAL

This application is a 371 of PCT/JP00/02700 filed Apr. 25, 2000.

FIELD OF THE INVENTION

The present invention relates to antimicrobial organic polymer materials capable of killing microorganisms, fungi, bacteria, viruses or the like in air or liquids.

PRIOR ART

Infectious diseases found on the medical field are known to often induce serious conditions and thought to be caused by antibiotic-resistant bacteria such as MRSA, VRSA and VRE or fungi, bacteria, viruses or the like. These are so-called nosocomial infections, which are not only contagious but also air-borne. Therefore, it is necessary to sterilize the outside air to be taken in or the inside air in closed spaces such as operating rooms, intensive care units or the like. The same problem occurs in closed spaces such as airplane cabins. A conventional means for sterilizing the air is an HEPA filter, which cannot be always an excellent sterilizing means because it suffers high air pressure losses and viruses pass through it and cannot be eliminated.

An object of the present invention is to solve these problems and to provide a filter material capable of killing microorganisms, fungi, bacteria, viruses or the like in the air or liquids.

DISCLOSURE OF THE INVENTION

It is well known that iodine has high antiseptic activity. For example, aqueous solutions of polyvinyl pyrrolidone carrying triiodide ion (povidone iodine) are widely used as antiseptics or mouth washers. However, povidone iodine shows high water solubility so that filter materials simply impregnated with this substance cannot serve as antimicrobial filters because the absorbed povidone iodine is totally released as soon as a liquid to be treated is passed through such filters. As a result of careful studies to provide a filter material fulfilling the above object by using this highly aseptic iodine, we accomplished the present invention on the basis of the finding that an antimicrobial organic polymer material capable of gradually releasing iodine molecules in triiodide ion into air or an aqueous medium to kill microorganisms can be provided by introducing a functional group capable of carrying triiodide ion ($I_3^{31}$) into a polymer side chain of an organic polymer material so that triiodide ion is carried on this polymer side chain via the functional group. As used herein, the term "antimicrobial" includes all of antimicrobial, antifungal, antibacterial, antiviral, etc.

Accordingly, the present invention relates to an antimicrobial organic polymer material comprising an organic polymer material having a polymer side chain containing a unit derived from an N-alkyl-N-vinylalkylamide on a backbone of a polymer substrate, wherein triiodide ion ($I_3^-$) is carried on said organic polymer material. As used herein, the expression "triiodide ion is carried" means that triiodide ion and $I_2$ form a polyiodine to provide an adduct as counter ion to be carried on the polymer side chain.

N-alkyl-N-vinylalkylamides such as N-vinylpyrrolidone are widely known to bind to iodine as described above. However, no attempt has been so far made to provide an antimicrobial material having triiodide ion carried on said N-alkyl-N-vinylalkylamide group introduced in the form of a polymer side chain into a polymer substrate such as a resin or a nonwoven fabric.

Generally when a functional group is introduced into an organic polymer to confer a specific function, the backbones are crosslinked to each other to compensate for the deterioration of physical strength caused by the introduction of this functional group. Typical examples thereof are ion exchange resins, in which an ion exchange group such as a sulfone or quaternary ammonium group is generally introduced into a polystyrene backbone obtained by polymerizing a styrene monomer. However, these ion exchange groups are hydrophilic groups that are bulky by the surrounding several coordinated water molecules so that the resins are insufficient in physical strength and dissolve even in water. In order to solve this problem with ion exchange resins, polystyrene backbones are crosslinked to each other with a crosslinker such as divinylbenzene. This enhances physical strength of the resins, which no more dissolve in water, but the formation of a crosslinked structure impairs absorption/desorption functions such as absorption speed or diffusion speed. This problem also occurs when an N-alkyl-N-vinylalkylamide is introduced into a backbone of an organic polymer substrate. That is, polymer materials cannot hold physical strength when an N-alkyl-N-vinylalkylamide group is directly introduced onto a polymer backbone, but their adsorption function is deteriorated if polymer backbones are crosslinked to each other for holding physical strength.

According to the present invention it was found that an N-alkyl-N-vinylalkylamide group can be introduced into an organic polymer substrate while holding the physical strength of the polymer backbones by attaching a side chain in the form of a polymer chain containing a unit derived from the N-alkyl-N-vinylalkylamide onto a polymer backbone of the organic polymer substrate. The present invention will now be further explained in detail.

THE MOST PREFERRED EMBODIMENTS OF THE INVENTION

Figure 1:
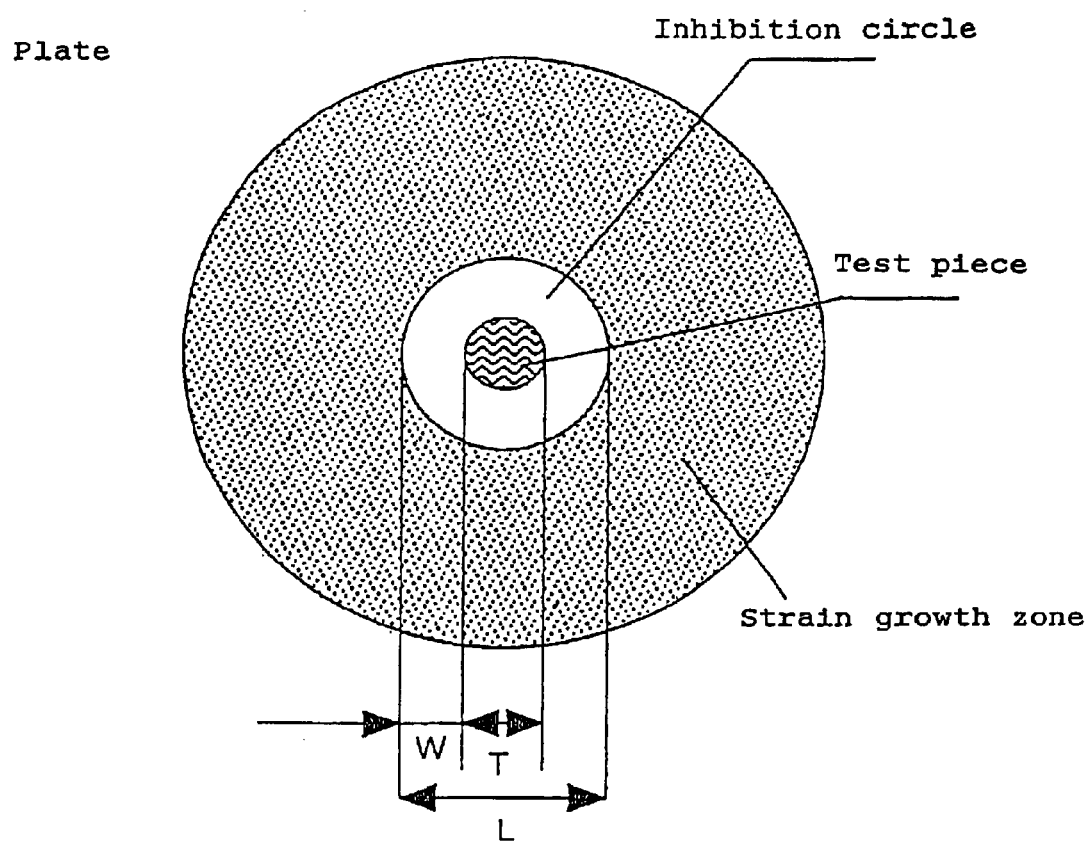
FIG. 1 schematically shows the antibacterial activity assay in the example of the present invention.

In antimicrobial organic polymer materials of the present invention, suitable means for introducing a side chain in the form of a polymer chain containing a unit derived from an N-alkyl-N-vinylalkylamide onto a backbone of an organic polymer substrate include graft polymerization. Especially, radiation-induced graft polymerization is the most preferred method for the purpose of the present invention, because it is a method that permits a desired graft polymer side chain to be introduced into a polymer substrate by irradiating the substrate to produce a radical and reacting it with a graft monomer and characterized in that the number or length of the graft chain can be relatively freely controlled and the polymer side chain can be introduced into existing polymer materials in various shapes.

In the present invention, materials that can be used as substrates into which is introduced a side chain in the form of a polymer chain containing a unit derived from an N-alkyl-N-vinylalkylamide include woven and nonwoven fabrics composed of a polymer fiber or an assembly thereof. Woven/nonwoven fabric substrates are preferred materials for antimicrobial filters because they can be conveniently used as substrates for radiation-induced graft polymerization and are light and easy to process.

Radiations that can be used In radiation-Induced graft polymerization well suitable for the purpose of the present invention include α-rays, β-rays, γ-rays, electron rays, UV ray, etc., among which γ-rays and electron rays are preferred for use in the present invention. Radiation-induced graft polymerization includes pre-irradiation graft polymerization involving preliminarily irradiating a graft substrate and then bringing it into contact with a polymerizable monomer (graft monomer) for reaction, and simultaneous irradiation graft polymerization involving simultaneously irradiating a substrate and a monomer, both of which can be used in the present invention. Radiation-induced graft polymerization also includes various manners of contact between a monomer and a substrate, such as liquid phase graft polymerization performed with a substrate immersed in a monomer solution gas phase graft polymerization performed with a substrate in contact with the vapor of a monomer, or immersion gas phase graft polymerization performed by immersing a substrate in a monomer solution and then removing it from the monomer solution for reaction in a gas phase, any of which can be used in the present invention.

Fiber or a woven/nonwoven fabric which is a fiber assembly is the most preferred materials for use as antimicrobial polymer materials of the present invention, and are well suitable for use in the immersion gas phase graft polymerization because they tend to retain monomer solutions.

Organic polymer substrates for antimicrobial polymer materials of the present invention are preferably polyolefin-based organic polymer materials. Polyolefin-based organic polymer materials are suitable for the purpose of introducing a graft side chain by radiation-induced graft polymerization because they are not disintegratable by radiation. When antimicrobial polymer materials of the present invention are used as filter materials, a fiber or a woven/nonwoven fabric which is a fiber assembly or processed products thereof are preferably used as substrates.

In the present invention, a polymerizable monomer containing an N-alkyl-N-vinylalkylamide is graft polymerized on a backbone of an organic polymer substrate to prepare an organic polymer material having a polymer side chain containing a unit derived from the N-alkyl-N-vinylalkylamide on the backbone of the polymer substrate, and triiodide ion is carried thereon. Specific examples of compounds that can be used as polymerizable monomers for this purpose include one or more polymerizable monomers selected from N-vinylpyrrolidone, 1-vinyl-2-piperidone, N-vinyl-N-methylacetamide. N-vinyl-N-ethylacetamide, N-vinyl-N-methyl propylamide, N-vinyl-N-ethyl propylamide and derivatives thereof.

Antimicrobial organic polymer materials of the present invention have a polymer side chain containing a unit derived from an N-alkyl-N-vinylalkylamide introduced onto a backbone of an organic polymer substrate, and triiodide ion ($I_3^-$) is carried on the N-alkyl-N-vinylalkylamide group present on this side chain, as described above.

In order to load triiodide ion, an organic polymer material having a polymer side chain containing a unit derived from an N-alkyl-N-vinylalkylamide on a backbone of a polymer substrate as described above can be brought into contact with triiodide ion by immersing the polymer material in an aqueous iodine/potassium iodide solution or an aqueous iodine/hydrogen iodide solution or passing said solution through a filter made of the polymer material, for example. Triiodide ion can also be carried on a polymer material by bringing the vapor of iodine into contact with the polymer material immersed in an aqueous iodine/potassium iodide solution or placing a similarly immersed polymer material on iodine powder and bringing the vapor of iodine emitted from the iodine powder into contact with the polymer material.

Triiodide ion can also be carried on a polymer material by immersing the polymer material in a solution of iodine dissolved in an organic solvent such as dichloromethane, chloroform or methanol, and adding hydroiodic acid to the solution.

The amount of triiodide ion to be carried on a polymer material varies with the nature of the medium to be sterilized, the amount of the microorganism to be eliminated such as bacteria, the operation environment of the polymer material, the shape of the polymer material, etc. but a preferred range is typically about 1–30% per unit weight of the polymer material.

As an example, a reaction for forming an antimicrobial polymer material of the present invention by graft polymerizing N-vinylpyrrolidone to a polymer substrate composed of a polyethylene nonwoven fabric via radiation-induced graft polymerization to form a polymer side chain containing a unit derived from N-vinylpyrrolidone and immersing said grafted polymer in an acidic iodine/potassium iodide solution seems to proceed as shown below.

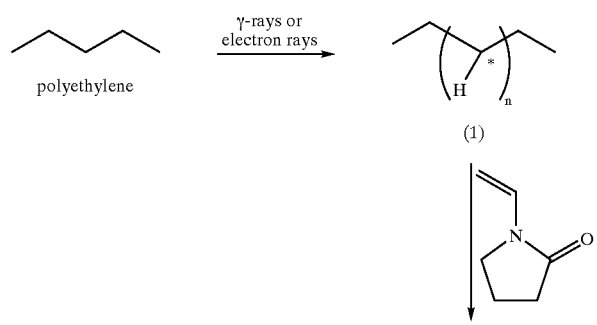

(1)

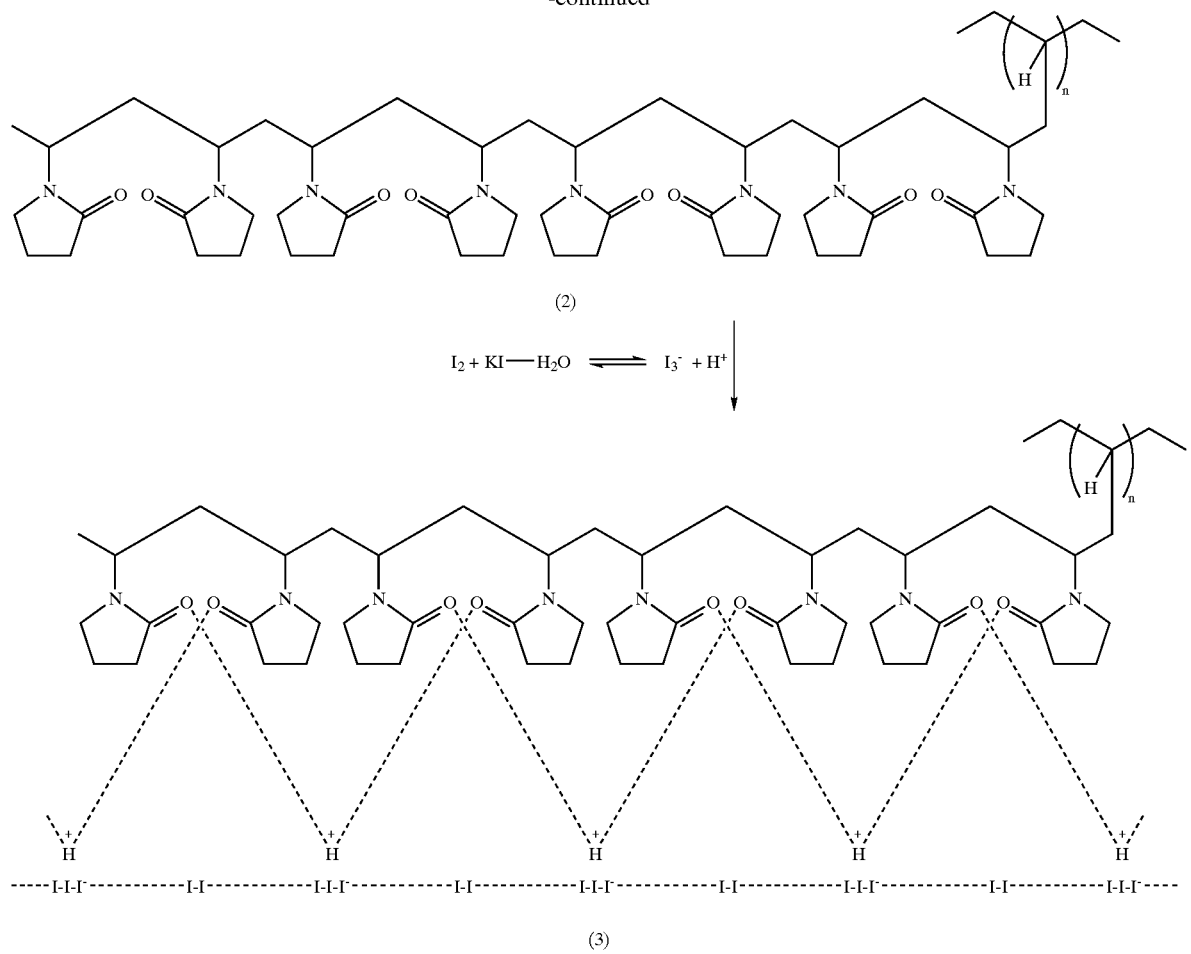

(2)

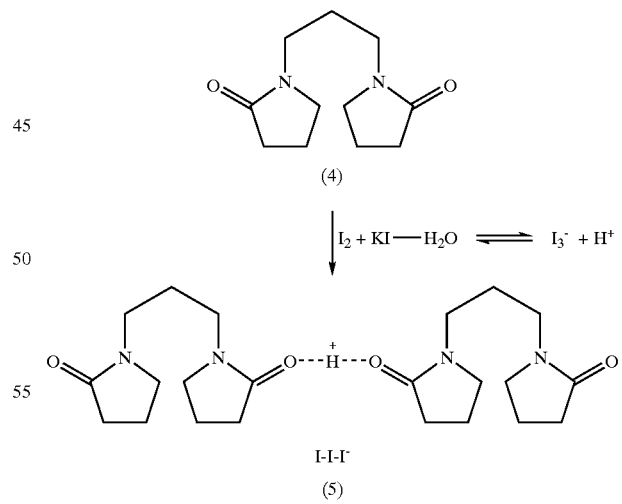

(3)

In order to explain the above structure, we prepared a dimer of N-vinylpyrrolidone (represented by formula (4) below) and determined the resonance Raman spectrum of a compound (represented by formula (5) below) obtained by reacting said dimer with an acidic iodine/potassium iodide solution, which showed absorption of $I_3^-$ at 107.7 cm$^{-1}$. The X-ray crystal structure analysis of the resulting compound showed that it has a structure containing intermolecular hydrogen bonds as shown in formula (5) below but not intramolecular hydrogen bonds. This was also proved by the molecular orbital calculation using PM3 hamiltonian showing that intermolecular hydrogen bonds are more stable than intramolecular hydrogen bonds. This result shows that no hydrogen bond occurs between adjacent pyrollidone units in the compound of formula (3) above. The resonance Raman spectrum of compound (3) prepared according to the scheme shown above showed absorption of $I_3^-$ at 110.7 cm$^{-1}$ and absorption of $I_2$, at 166.7 cm$^{-1}$. These results proved that triiodide ion $I_3^-$ is combined with iodine $I_2$ to form a polyiodine:

which provides a counter ion adduct carried on antimicrobial polymer materials of the present invention as shown in formula (3) above.

Antimicrobial polymer materials of the present invention have triiodide ion in the form of a polyiodine carried on a polymer side chain containing a unit derived from an N-alkyl-N-vinylalkylamide present on a backbone of a polymer substrate as described above, so that if such materials are used as filters for liquid through which a liquid to be treated containing bacteria or viruses is passed, iodine ($I_2$) is liberated from the polyiodine carried on the filters to kill the bacteria or viruses in the liquid to be treated and iodine in the polyiodine adduct gradually dissolves into the liquid to be treated to further kill the bacteria or viruses in the liquid to be treated. Antimicrobial polymer materials of the present invention can hold high antimicrobial activity for a long period because triiodide ion is carried as counter ion in the form of a polyiodine with iodine ($I_2$) as shown in the scheme above and thus slowly released. If antimicrobial polymer materials of the present invention are used as gas filters, iodine in the carried triiodide ion evaporates and diffuses in the gas to be treated to sterilize the gas to be treated. In this case, antimicrobial polymer materials of the present invention can also hold high antimicrobial activity for a long period because iodine shows slow-release characteristics.

Polymer materials carrying triiodide ion shows the color of iodine, which gradually fades as iodine is released. Thus, the carried amount of the remaining iodine, i.e., the remaining antimicrobial activity of antimicrobial polymer materials can be evaluated by the color density of the antimicrobial polymer materials. Taking advantage of this phenomenon, antimicrobial polymer materials of the present invention can be optically monitored for their antimicrobial activity. Monitoring can be made by visual observation or by measuring the absorption/reflection of iodine in the visible light range using a spectrophotometer. For example, antimicrobial polymer materials of the present invention can be considered to have consumed antimicrobial activity and replaced by fresh one or regenerated when they almost lose the color of iodine. The color density at which sufficient antimicrobial activity cannot be shown can be experimentally determined depending on various parameters such as the amount of iodine carried on the antimicrobial material, the shape or size of the antimicrobial material, conditions of the liquid or gas to be treated with the antimicrobial material, etc.

When antimicrobial polymer materials of the present invention can show no more sufficient antimicrobial activity after iodine in triiodide ion carried in the form of a polyiodine adduct is released, they can be conveniently regenerated by reloading triiodide ion on the antimicrobial polymer materials. Reloading of triiodide ion for regeneration can be performed in the same manner as for the preparation of antimicrobial polymer materials.

Antimicrobial polymer materials of the present invention can be in any of various shapes such as a woven/nonwoven fabric, plate member, bead member, bulk member, film, net or the like.

Antimicrobial polymer materials of the present invention can be used to sterilize any medium susceptible to the presence of microorganisms, bacteria or the like. For example, antimicrobial polymer materials of the present invention can be formed into a nonwoven fabric and used as air filters for sterilization/disinfection such as air filters for air-conditioners in hospitals, air filters for green houses, filters for safety cabinets or air filters for air-conditioning airplane cabins; antibacterial/antiviral filters for agricultural water, waste liquor, cooling tower water or sewage treatment plant water; water filters in culture ponds; filters for circulation bath tabs; or bandages or medical absorbent gauzes or masks. Antimicrobial polymer materials of the present invention can also be used in fumigation treatments by covering the soil with said materials in the form of a sheet or mixing said materials in the form of fiber chips into the soil.

As described above, antimicrobial organic polymer materials of the present invention comprise a polymer material having a polymer side chain containing at least a unit derived from an N-alkyl-N-vinylalkylamide on a backbone of a polymer substrate, wherein triiodide ion is carried in the form of a polyiodine on said polymer material, and they are very useful as antimicrobial materials for the air or liquids because they have high physical strength and can gradually release iodine in the triiodide ion carried in the form of a polyiodine. Antimicrobial organic polymer materials of the present invention lose their color as iodine in the carried triiodide ion is released, so that their remaining antimicrobial activity can be monitored by the color of the materials. In addition, their antimicrobial activity can be very conveniently regenerated by reloading triiodide ion when it has been consumed.

INDUSTRIAL APPLICATION

Antimicrobial organic polymer materials of the present invention are very useful as antimicrobial materials for use in environments susceptible to the presence of microorganisms or bacteria such as air filters for air-conditioners in hospitals, antibacterial/antiviral filters for agricultural water or filters for circulation bath tabs or water filters for culture ponds. Especially, they can be sufficiently applied to causal agents for nosocomial infections among recent issues such as MRSA, VRSA, VRE.

EXAMPLES

The following examples further illustrate the present invention without, however, limiting the same thereto.

Example 1

Preparation of an Antimicrobial Polymer Material

A nonwoven fabric having an areal density of 56 g/m$^2$ and a thickness of 0.2 mm which has been made of a polyethylene fiber of about 16 μm in diameter was used as a polymer substrate. This nonwoven fabric substrate was irradiated with γ-rays at 150 kGy in a nitrogen atmosphere and then immersed in an N-vinylpyrrolidone solution, which was heated for reaction to give an N-vinylpyrrolidone-grafted nonwoven fabric at a grafting degree of 134%. This grafted nonwoven fabric was cut into 15 cm×5 cm (0.1984 g in weight), thoroughly immersed in pure water and lightly drained, and then stirred for 1 hour in a mixed solution of 10 ml of 0.1 N iodine/potassium iodide solution or 0.1 N iodine/hydrogen iodide solution plus 190 ml of pure water. Then, it was immersed in 20 ml of 1 N hydrochloric acid solution for 10 minutes, and then washed with water, and the immersion solution of hydrochloric acid and the washing water were combined and titrated with 0.1 N $Na_2SO_3$ to assay the amount of iodine remaining in the solution, whereby the amount of iodine adsorbed to the nonwoven fabric material was determined. The resulting nonwoven fabric sample was dried and weighed (0.2725 g). The loading level of triiodide ion ($I_3^-$) was 1.40 mmol.

Example 2

Antibacterial Activity Assay

Test pieces in the form of a circle of 13 mm in diameter were stamped out from the nonwoven antimicrobial material prepared in Example 1. The strains tested were *Micrococcus luteus* ATCC 9341. *Bacillus anthracis* and *Escherichia coli* NIHJ. These strains maintained on slants were cultured on nutrient broth for 8 hours. The resulting cultures were partially collected and further cultured on nutrient broth for 18 hours. A dish was prepared containing 7 ml of nutrient agar sterilized by autoclaving and solidified. Nutrient broth containing 0.8% agar was sterilized by autoclaving and cooled to about 50° C., and 7 ml of this medium was mixed with each test strain cultured as above at a density of about $5 \times 10^6$ cells/ml and uniformly spread and solidified on said nutrient agar dish to prepare a plate, on which the test piece was placed and lightly pressed. As control samples, the polyethylene nonwoven fabric was cut into the same size as that of the test piece and placed on a similar plate without treatment or after impregnation with a polyvinyl pyrrolidone/iodine (povidone iodine) solution or an aqueous potassium iodide solution (0.05 mmol/l), and lightly pressed. The plate alone was also tested for confirming the growth of the strain.

Thus prepared plate samples were incubated for 24 hours in an incubator kept at 37° C. The diameter L (mm) of the growth inhibition circle formed around each test piece was measured. The inhibition circle width was calculated by the equation below:

$$W=(L-T)/2$$

where W=inhibition circle width; L=inhibition circle diameter (mm); T=test piece diameter (mm).

The inhibition circle width was the average of triplicate measurements on each test strain. Table 1 shows test results of the antimicrobial material of the present invention and Table 2 shows test results of control samples. FIG. 1 schematically shows the assay.

It was observed from Table 1 that the antimicrobial material of the present invention shows good antibacterial activity against each test strain. Said material kept the color of iodine after evaluation, i.e., iodine was not totally released during the test period of 24 hours, showing that it can be repeatedly used. No inhibition circle appeared in the control sample of an untreated polyethylene nonwoven fabric. The polyethylene nonwoven fabric impregnated with a povidone iodine solution and the polyethylene nonwoven fabric impregnated with an aqueous potassium iodide solution (0.05 mmol/l) totally lost the color of iodine and could not be repeatedly used though they showed antibacterial activity. The inhibition circle widths of these control samples were much smaller than that of the present invention, probably because the impregnated iodine was very rapidly released and evaporated and lost during the test period of 24 hours.

Example 3

Antifungal Activity Assay

The test strain was Candida albicans 3143. The strain maintained on slants was cultured on nutrient broth for 8 hours. The resulting cultures were partially collected and further cultured on nutrient broth for 18 hours. A dish was prepared containing 7 ml of nutrient agar sterilized by autoclaving and solidified. Complete medium for fungi containing 0.8% agar was sterilized by autoclaving and cooled to about 50° C., and 7 ml of this medium was mixed with the test strain cultured as above at a density of about $5 \times 10^6$ cells/ml and uniformly spread and solidified on said nutrient agar dish to prepare a plate, on which the test piece was placed and lightly pressed. As a control sample, the polyethylene nonwoven fabric was cut into the same size as that of the test piece and placed on a similar plate and lightly pressed. The plate alone was also tested for confirming the growth of the strain. The plate samples were incubated for 24 hours in an incubator to calculate the width of the growth inhibition circle in the same manner as in Example 2. The results are shown in Table 1

It was observed from Table 1 that the antimicrobial material of the present invention shows good antifungal activity. Said material kept the color of iodine after evaluation, i.e., triiodide ion was not totally released during the test period of 24 hours, showing that it can be repeatedly used. No inhibition circle appeared in the polyethylene nonwoven fabric and the plate alone (control samples).

TABLE 1

| Strain | Antibacterial activity | | | Antifungal activity Candida albicans |
|---|---|---|---|---|
| | Micrococcus luteus ATCC 9341 | Bacillus anthracis | E. coli NIHJ | |
| Cell density (cells/ml) | $5.0 \times 10^6$ | $5.0 \times 10^6$ | $5.0 \times 10^6$ | $5.0 \times 10^6$ |
| Inhibition circle width (mm) | 14.8 ± 0.3 | 18.0 ± 3.1 | 12.8 ± 1.8 | 3.7 ± 0.5 |

Note:
Test piece diameter = 13 mm

TABLE 2

Control test results

| Test material | Antibacterial activity | | |
|---|---|---|---|
| | Poly-ethylene | Polyethylene + PVP/I$_2$ | Polyethylene + iodine solution (0.05 mmol/l) |
| Cell density (cells/ml) | $5.0 \times 10^6$ | $5.0 \times 10^6$ | $5.0 \times 10^6$ |
| Inhibition circle width (mm) | 0 | 0.92 ± 0.14 | 1.58 ± 0.52 |

Note:
Test piece diameter = 13 mm;
Test strain = *Micrococcus luteus* ATCC 9341

What is claimed is:

1. An antimicrobial organic polymer material comprising an organic polymer having a polymer side chain containing one or more polymerized N-alkyl-N-vinylalkylamide monomer units bonded to the backbone of the organic polymer and triiodide ion, wherein the triiodide ion is carried on said organic polymer.

2. The antimicrobial organic polymer material of claim 1 wherein the polymer side chain has been introduced onto the backbone of the organic polymer by radiation-induced graft polymerization.

3. The antimicrobial organic polymer material of claim 1 wherein the side chain comprises one or more polymerized monomers selected from the group consisting of N-vinylpyrrolidone, 1-vinyl-2-piperidone, N-vinyl-N-methylacetamide, N-vinyl-N-ethylacetamide, N-vinyl-N-methyl propylamide, N-vinyl-N-ethyl propylamide.

4. The antimicrobial organic polymer material of claim 1 wherein the organic polymer comprises a polyolefin-based organic polymer.

5. The antimicrobial organic polymer material of claim 1 in the form selected from the group consisting of a fiber, a woven/nonwoven fabric which is a fiber assembly, processed products of the woven/nonwoven fabric, fiber chips, beads, nets, films, plate members and bulk members.

6. An antimicrobial filter comprising the antimicrobial organic polymer material of claim 1.

7. A process for preparing an antimicrobial organic polymer material, comprising introducing a polymer side chain containing one or more polymerized N-alkyl-N-vinylalkylamide monomer units onto the backbone of an organic polymer to form an organic polymer material; and loading triiodide ion on the organic polymer material.

8. The process of claim 7 wherein the polymer side chain is formed by graft-polymerizing a polymerizable monomer containing an N-alkyl-N-vinylalkylamide onto the backbone of an organic polymer by radiation-induced graft polymerization.

9. The antimicrobial organic polymer material of claim 1, wherein the organic polymer is a polyethylene polymer.

10. The antimicrobial organic polymer material of claim 1, wherein the side chain comprises one or more polymerized N-vinyl pyrrolidone monomers.

11. The process as claimed in claim 7, wherein the triiodide ion is loaded on the organic polymer material by immersing the organic polymer material in at least one of an aqueous iodine/potassium iodide solution or an aqueous iodine/hydrogen iodide solution.

12. The process as claimed in claim 7, wherein the triiodide ion is loaded onto the organic polymer material by passing a solution of at least one of aqueous iodine/potassium iodide or aqueous iodine/thydrogen iodide through a filter made of the organic polymer material.

13. The process of claim 7, wherein the triiodide ion is loaded on the organic polymer material by contacting the polymer material with iodine vapor.

14. The process of claim 7, wherein the triiodide ion is loaded on the organic polymer material by immersing the polymer material in a solution of iodine dissolved in an organic solvent.

15. The process as claimed in claim 14, wherein the organic solvent is at least one selected from the group consisting of dichloromethane, chloroform, and methanol.

16. The process as claimed in claim 14, further comprising:

adding hydroiodic acid to the solution.

17. The antimicrobial organic polymer material of claim 1, wherein the triiodide ion is present in an amount of from 1 to 30% per unit weight of the organic polymer.

18. An antimicrobial organic polymer material having graft chains on the backbone of a polymer substrate, the graft chains being obtained by graft polymerizing N-alkyl-N-vinylalkylamide to the polymer substrate, wherein triiodide ion is carried on said organic polymer material.

19. The antimicrobial organic polymer material of claim 18 wherein the graft chains are obtained by radiation-induced graft polymerizing N-alkyl-N-vinylalkylamide to the polymer substrate.

20. The antimicrobial organic polymer material of claim 18 wherein the N-alkyl-N-vinylalkylamide is at lest one selected from the group consisting of N-vinylpyrrolidone, 1-vinyl-2-piperidone, N-vinyl-N-methylacetamide, N-vinyl-N-ethylacetamide, N-vinyl-N-methyl propylamide, N-vinyl-N-ethyl propylamide.

21. The antimicrobial organic polymer material of claim 18 wherein the polymer substrate is a polyolefin-based organic polymer.

22. The antimicrobial organic polymer material of claim 18 in the form selected from the group consisting of a fiber, a woven/nonwoven fabric which is a fiber assembly and processed products thereof, fiber chips, beads, nets, films, plate members and bulk members.

23. An antimicrobial filter comprising the antimicrobial organic polymer material of claim 18.

24. A process for preparing an antimicrobial organic polymer material, comprising graft polymerizing N-alkyl-N-vinylalkylamide to a polymer substrate and loading triiodide on the resulting polymer material.

25. The process of claim 24 wherein the graft polymerization is radiation-induced graft polymerization.

* * * * *